US011565058B2

(12) United States Patent
Peng

(10) Patent No.: US 11,565,058 B2
(45) Date of Patent: Jan. 31, 2023

(54) ELECTRONIC CIGARETTE ATOMIZER AND ELECTRONIC CIGARETTE

(71) Applicant: SHENZHEN MASON VAP TECHNOLOGY CO., LTD., Shenzhen (CN)

(72) Inventor: Shijian Peng, Shenzhen (CN)

(73) Assignee: SHENZHEN MASON VAP TECHNOLOGY CO., LTD., Shenzhen (CN)

( * ) Notice: Subject to any disclaimer, the term of this patent is extended or adjusted under 35 U.S.C. 154(b) by 659 days.

(21) Appl. No.: 16/546,804

(22) Filed: Aug. 21, 2019

(65) Prior Publication Data

US 2020/0094000 A1  Mar. 26, 2020

(30) Foreign Application Priority Data

Sep. 25, 2018 (CN) .................... 201821567201.X

(51) Int. Cl.
  *A61M 11/04* (2006.01)
  *A24F 40/44* (2020.01)
  *A24F 40/40* (2020.01)
  *A24F 40/10* (2020.01)
  *F17C 9/02* (2006.01)

(52) U.S. Cl.
  CPC .......... *A61M 11/044* (2014.02); *A24F 40/10* (2020.01); *A24F 40/40* (2020.01); *A24F 40/44* (2020.01); *A61M 2205/8206* (2013.01); *F17C 9/02* (2013.01)

(58) Field of Classification Search
  CPC ....... A61M 11/044; A24F 40/00; A24F 40/20; A24F 40/40
  See application file for complete search history.

(56) References Cited

U.S. PATENT DOCUMENTS

| | | | | |
|---|---|---|---|---|
| 2015/0359262 | A1* | 12/2015 | Liu | ..................... C04B 35/6263 264/681 |
| 2016/0015081 | A1* | 1/2016 | Liu | .......................... H05B 3/16 131/329 |
| 2017/0325504 | A1* | 11/2017 | Liu | ....................... A61M 11/042 |
| 2018/0162769 | A1* | 6/2018 | Peuchert | .................. C03C 11/00 |
| 2021/0161207 | A1* | 6/2021 | Li | ............................. H05B 3/10 |

* cited by examiner

*Primary Examiner* — Alex B Efta
(74) *Attorney, Agent, or Firm* — Fleit Intellectual Property Law; Paul D. Bianco

(57) ABSTRACT

The disclosure discloses an electronic cigarette atomizer and an electronic cigarette, including an outer casing, wherein the outer casing is provided inside with an atomization cavity, a gas outlet is provided at a top end of the atomization cavity, a gas inlet is provided at a bottom end of the atomization cavity, the atomization cavity is provided inside with an atomization assembly, and the atomization assembly includes an oil guiding cotton swab, an electric heating wire wound around outer periphery of the oil guiding cotton swab, and an oil guiding cotton cloth layer covering the top of the oil guiding cotton swab.

10 Claims, 13 Drawing Sheets

ELECTRONIC CIGARETTE ATOMIZER AND ELECTRONIC CIGARETTE

CROSS-REFERENCE TO RELATED APPLICATIONS

The present disclosure claims the priority of the Chinese Patent Application No. 201821567201.X, entitled "An Electronic Cigarette Atomizer and Electronic Cigarette", filed with the Chinese Patent Office on Sep. 25, 2018, the content of which is incorporated herein by reference in its entirety.

TECHNICAL FIELD

The disclosure relates to the technical field of electronic cigarettes, and in particular to an electronic cigarette atomizer and an electronic cigarette.

BACKGROUND ART

With the development of the society, people are paying more and more attention to their own health, the number of people who smoke is gradually decreasing, and as a substitute for cigarette, electronic cigarette has been rapidly popularized in the market; and as a major component of the electronic cigarette, an atomization core is used to atomize cigarette oil and for the atomized cigarette oil to mix with gas.

However, the atomization assembly in the electronic cigarette atomizer on the market today comprises an electric heating wire and an oil guiding cotton swab, the electric heating wire is wound around the oil guiding cotton swab, the cigarette oil is guided from two ends of the oil guiding cotton swab toward the middle of the electric heating wire, and the electric heating wire is powered on and heated to atomize the cigarette oil.

The electric heating wire has the highest temperature at the middle position when heated, the cigarette oil is supplied from two ends of the oil guiding cotton swab toward the middle, the oil content at two ends of the oil guiding cotton swab is greater than that in the middle, and the oil content in the middle of the oil guiding cotton swab is minimum, and if the oil content in the middle of the oil guiding cotton swab lacks, the scorching phenomenon will occur; and if oil content at two ends of the oil guiding cotton swab exceeds, there will be oil leakage.

If the oil content at two ends of the oil guiding cotton swab meets "no oil leakage" and reaches an equilibrating oil quantity, the oil content in the middle of the oil guiding cotton swab will be less than the equilibrating oil quantity. Moreover, the amount of heat generated at the middle position of the electric heating wire is maximum, which easily leads to scorching of the cotton or the cigarette oil, and thus poor taste.

If the oil content in the middle of the oil guiding cotton swab meets "no scorching" and "no oil leakage", and reaches the equilibrating oil quantity, the oil content at two ends of the oil guiding cotton swab will be greater than the equilibrating oil quantity, increasing the risk of oil leakage.

In summary, the electronic cigarette atomizer on the market today involves a problem that oil is supplied from two ends of the oil guiding cotton swab toward the middle of the oil guiding cotton swab, resulting in unbalanced distributions of the oil content of the oil guiding cotton swab, thus resulting in unbalanced speed of supplying oil to the electric heating wire, where the unbalanced oil supply also causes unbalanced surface heating temperature of the electric heating wire, eventually leading to the issue of poor taste of the atomized cigarette oil.

SUMMARY

Specifically, the disclosure proposes the following specific implementations:

An electronic cigarette atomizer, comprising: an outer casing, wherein the outer casing is provided inside with an atomization cavity, a gas outlet is provided at a top end of the atomization cavity, and a gas inlet is provided at a bottom end of the atomization cavity, an atomization assembly is provided in the atomization cavity, and the atomization assembly comprises an oil guiding cotton swab, an electric heating wire wound around outer periphery of the oil guiding cotton swab, and an oil guiding cotton cloth layer covering the top of the oil guiding cotton swab.

The disclosure further provides an electronic cigarette, comprising the above-mentioned atomizer.

DESCRIPTION OF THE DRAWINGS

To illustrate the technical solution of the embodiment of the disclosure more clearly, drawings required for use in the embodiments will be introduced briefly below. It should be understood that the following drawings show only some embodiments of the disclosure and therefore should not be considered as a limitation to the scope, and those ordinary skilled in the art may obtain other related drawings in the light of these drawings without any inventive labor.

REFERENCE SIGNS

Figure 1:
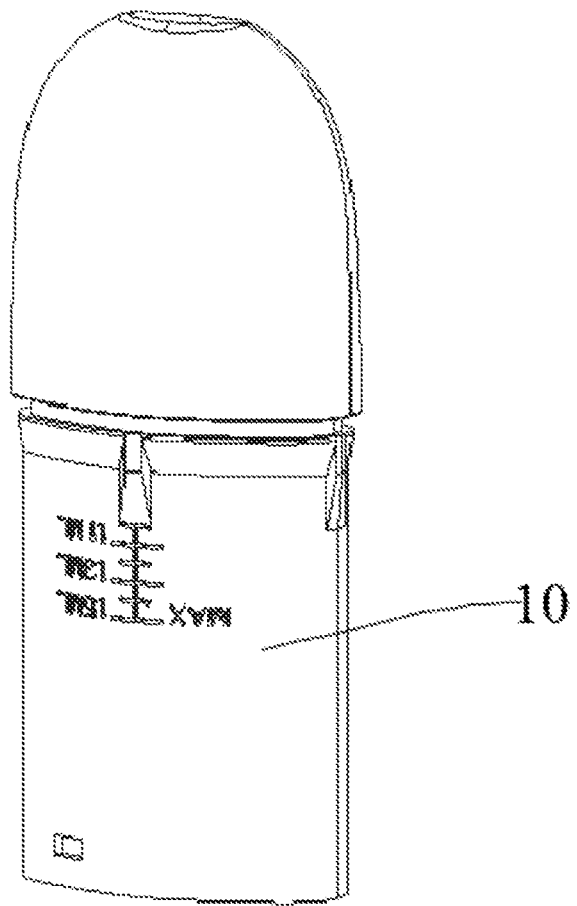
FIG. 1 is an isometric view of an electronic cigarette atomizer of an embodiment of the disclosure.
Figure 2:
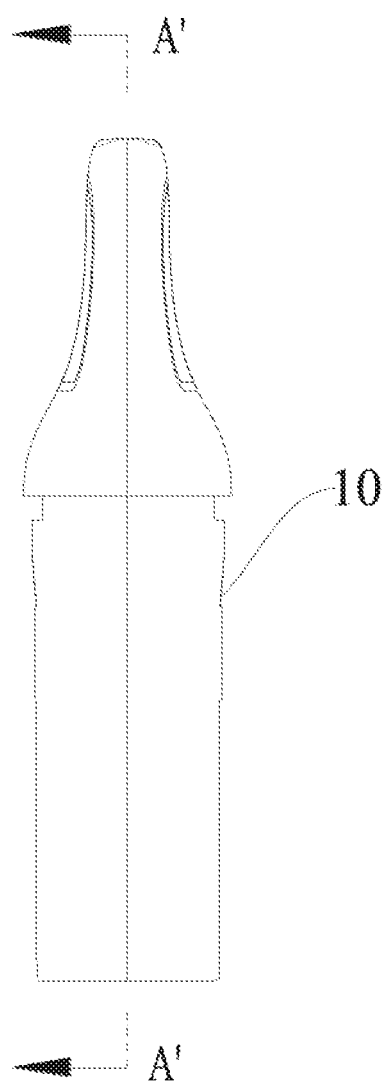
FIG. 2 is a left view of an electronic cigarette atomizer of an embodiment of the disclosure.

10—outer casing;
100—atomization cavity;
110—gas outlet;
120—gas inlet;
130—atomization assembly;
131—oil guiding cotton swab;
132—electric heating wire;
133—oil guiding cotton cloth layer;

140—oil supply channel;
141—oil inlet end;
142—oil outlet end;
150—first electrode;
160—second electrode;
170—first groove;
180—lower base;
181—second groove;
182—hollow channel;
183—first clamping slot;
190—upper base;
191—second clamping slot;
200—oil storage cavity; and
300—gas guiding channel.

DETAILED DESCRIPTION OF THE EMBODIMENTS

To facilitate an understanding of the disclosure, an electronic cigarette atomizer will be described more comprehensively hereinafter with reference to the related drawings. A preferred embodiment of electronic cigarette atomizer is shown in the drawings. However, the electronic cigarette atomizer can be implemented in many different forms and is not limited to the embodiments described herein. Instead, the objective of providing these embodiments is to make the disclosure of electronic cigarette atomizer more thorough and comprehensive.

In the following, the term "comprise" or "may comprise" that may be used in the various embodiments of the disclosure indicates the presence of the disclosed function, operation or element, and does not limit an addition of one or more functions, operations or elements. Moreover, as used in various embodiments of the disclosure, the terms "comprise", "have" and derivatives thereof only intend to denote particular features, numbers, steps, operations, elements, assemblies, or combinations of the foregoing, and should not to be construed as first excluding probabilities of the presence of one or more other features, numbers, steps, operations, elements, assemblies, or combinations of the foregoing, or addition of one or more features, numbers, steps, operations, elements, assemblies, or combinations of the foregoing.

In various embodiments of the disclosure, the expression "or" or "at least one of A or/and B" includes any and all combinations of the words listed simultaneously. For example, the expression "A or B" or "at least one of A or/and B" may include A, may include B, or may include both A and B.

In the description of the disclosure, it should be understood that orientation or positional relations indicated by terms such as "longitudinal", "transversal", "upper", "lower", "front", "rear", "left", "right", "vertical", "horizontal", "top", "bottom", "inside" and "outside" are based on the orientation or positional relations as shown in the drawings, only for facilitating description of the disclosure and simplifying the description, rather than indicating or implying that the referred devices or elements must be in a particular orientation or constructed or operated in the particular orientation, and therefore they should not be construed as limiting the disclosure. In addition, terms such as "first", "second", and "third" are used only for distinguishing the description, and should not be understood as indicating or implying to have importance in relativity.

In the description of the specification, the description with reference to the terms "one embodiment", "some embodiments", "example", "specific example", or "some examples" and the like means that specific features, structures, materials or characteristics described in connection with the embodiment or the example are included in at least one embodiment or example of the disclosure. In the specification, the schematic representation of the above-mentioned terms does not necessarily mean the same embodiment or example. Furthermore, the specific features, structures, materials, or characteristics described may be combined in a suitable manner in any one or more embodiments or examples.

In the description of the disclosure, it should be indicated that unless otherwise specified or defined, terms "mount", "link" or "connect" should be understood broadly, and for example, a connection may be a mechanical connection or an electric connection, may also be an internal communication between two elements, may be a direct linking, or an indirect linking via an intermediate medium. The specific meanings of the above-mentioned terms could be understood by those ordinarily skilled in the art according to specific situations. Unless otherwise defined, all terms (including technical and scientific terms) used herein have the same meaning as commonly understood by those ordinarily skilled in the field of the various embodiments of the disclosure. The term (such as a term defined in a commonly used dictionary) will be construed as having the same meaning as the contextual meaning in the related art and will not be construed as having an idealized meaning or an overly formal meaning, unless clearly defined in the various embodiments of the disclosure.

The disclosure provides an electronic cigarette atomizer and electronic cigarette, which better overcome problems and defects existing in the above-mentioned prior art, wherein the electronic cigarette atomizer has a simple structure and a reasonable design, the atomization assembly of the electronic cigarette atomizer comprises an oil guiding cotton swab, an electric heating wire wound around outer periphery of the oil guiding cotton swab, and an oil guiding cotton cloth layer covering the top of the oil guiding cotton swab; and the oil guiding cotton swab can absorb cigarette oil from the entire section of the above oil guiding cotton cloth layer, such that the entire section of the oil guiding cotton swab can supply oil to the electric heating wire in a balanced manner, and the oil guiding cotton cloth layer and the oil guiding cotton swab can also simultaneously supply oil to the electric heating wire. The "number of oil-containing molecules on the oil supply contact surface" required by normal working is YL, which is a product of the oil supply contact area S and the number L of oil-containing molecules per unit area, that is, YL=S*L. The oil content of the oil guiding cotton cloth layer and the oil guiding cotton swab of the atomization assembly of the electronic cigarette atomizer easily reaches a balanced distribution on the one hand, and the oil supply contact area S for the electric heating wire is also increased on the other hand, the oil is supplied by adhering to the surface of the electric heating wire in multiple directions at close-range, and the entire section of the electric heating wire is supplied with oil in a balanced and rapid manner. In this way, not only the number L of oil-containing molecules per unit area of the oil guiding cotton cloth layer and the oil guiding cotton swab is reduced accordingly, effectively reducing the risk of oil leakage, but also the surface heating temperature of the entire section of the electric heating wire is balanced, effectively solving the problem of scorching the cotton and cigarette oil, thereby effectively solving the problem of poor taste of atomized cigarette oil.

Specifically, the disclosure proposes the following specific implementations:

An electronic cigarette atomizer, comprising: an outer casing, wherein the outer casing is provided inside with an atomization cavity, a gas outlet is provided at a top end of the atomization cavity, and a gas inlet is provided at a bottom end of the atomization cavity, an atomization assembly is provided in the atomization cavity, and the atomization assembly comprises an oil guiding cotton swab, an electric heating wire wound around outer periphery of the oil guiding cotton swab, and an oil guiding cotton cloth layer covering the top of the oil guiding cotton swab.

Further, an oil storage cavity is provided inside the outer casing, with the oil storage cavity located above the atomization cavity, two ends of the top of the atomization cavity each are provided with an oil supply channel, oil inlet ends of the two oil supply channels each are in communication with the oil storage cavity, and oil outlet ends of the two oil supply channels are respectively connected with upper surfaces of two ends of the oil guiding cotton cloth layer.

Further, a gas guiding channel is provided inside the outer casing, in the middle of the oil storage cavity, and the gas guiding channel is in communication with the gas outlet.

Further, a first electrode and a second electrode are provided in the atomization cavity, the first electrode is electrically connected to one end of the electric heating wire, and the second electrode is electrically connected to the other end of the electric heating wire.

Further, the gas inlet comprises a plurality of micropores provided at a bottom end of the atomization cavity, the cross-sectional area of each micropore is less than or equal to 0.785 mm$^2$; and a first groove is provided in the middle of an inner side of the bottom end of the atomization cavity.

Further, a lower base is provided in the atomization cavity, the lower base configured for supporting the atomization assembly.

Further, a second groove and a hollow channel communicating the second groove with the first groove are provided in the middle of the lower base and located below the atomization assembly, and a gas flow channel is provided between a bottom of the hollow channel and the gas inlet.

Further, an upper base is provided inside the atomization cavity, with the upper base located above the lower base, the atomization assembly is fixed between the upper base and the lower base, and there are gas flow channels communicating with each other between two sides of the upper base and inner walls of the atomization cavity, between the top of the upper base and the gas outlet, and between the bottom of the upper base and the top of the second groove.

Further, a first clamping slot is provided at two ends of the top of the lower base, and two ends of the oil guiding cotton swab are erected on the first clamping slot; and the upper base is provided with a second clamping slot for accommodating the oil guiding cotton cloth layer.

The disclosure further provides an electronic cigarette, comprising the above-mentioned atomizer.

To understand the above-mentioned objects, features and advantages of the disclosure more easily, detailed descriptions will be made as follows with respect better embodiments illustrated in detail hereinafter in conjunction with the accompanying drawings.

EXAMPLE

Referring to FIGS. 1 to 7, the disclosure provides an electronic cigarette atomizer, comprising an outer casing 10, wherein the outer casing 10 is provided inside with an atomization cavity 100, a gas outlet 110 is provided at a top end of the atomization cavity 100, and a gas inlet 120 is provided at a bottom end of the atomization cavity 100, an atomization assembly 130 is provided in the atomization cavity 100, the atomization assembly 130 comprises an oil guiding cotton swab 131, an electric heating wire 132 wound around outer periphery of the oil guiding cotton swab 131, and an oil guiding cotton cloth layer 133 covering the top of the oil guiding cotton swab 131.

It should be noted that gas enters from the gas inlet 120, and takes the smoke generated by the atomization assembly 130 out through the gas outlet 110. The oil guiding cotton swab 131 is of a cylindrical-like shape, and preferably, an upper half of the oil guiding cotton swab 131 is in direct contact with the oil guiding cotton cloth layer 133, and the length of the oil guiding cotton swab 131 is the same as or slightly smaller than the length of the oil guiding surface layer, the oil guiding cotton swab 131 enables to absorb cigarette oil from the entire section of the above oil guiding cotton cloth layer 133, so that the entire section of the oil guiding cotton swab 131 can supply oil to the electric heating wire 132 in a balanced manner, and the oil guiding cotton cloth layer 133 and the oil guiding cotton swab 131 can also supply oil to the electric heating wire 132 simultaneously. The "number of oil-containing molecules on the oil supply contact surface" required by normal working is YL, which is a product of the oil supply contact area S and the number L of oil-containing molecules per unit area, that is, $YL=S*L$. The oil content of the oil guiding cotton cloth layer 133 and the oil guiding cotton swab 131 of the atomization assembly 130 of the electronic cigarette atomizer easily reaches a balanced distribution on the one hand, and the oil supply contact area S for the electric heating wire 132 is also increased on the other hand, and the oil is supplied by adhering to the surface of the electric heating wire 132 in multiple directions at close-range, the entire section of the electric heating wire 132 is supplied with oil in a balanced and rapid manner. In this way, not only the number L of oil-containing molecules per unit area of the oil guiding cotton cloth layer 133 and the oil guiding cotton swab 131 is reduced accordingly, effectively reducing the risk of oil leakage, but also the surface heating temperature of the entire section of the electric heating wire 132 is balanced, effectively solving the problem of scorching the cotton and cigarette oil, thereby effectively solving the problem of poor taste of atomized cigarette oil.

Figure 3:
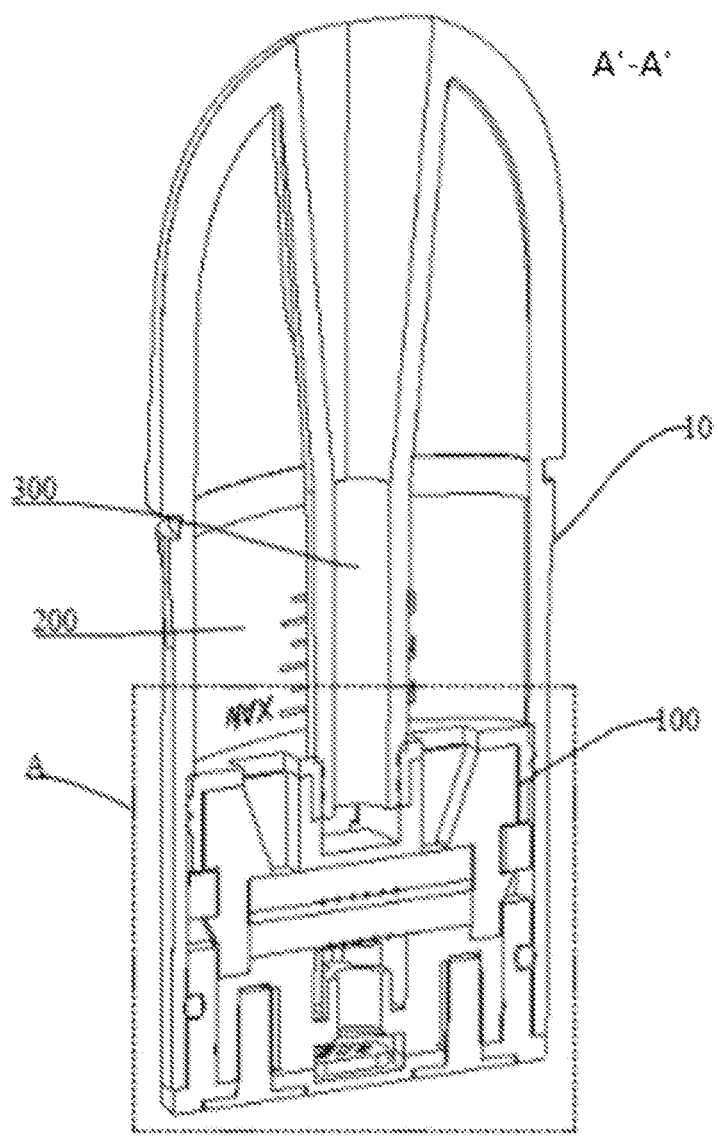
FIG. 3 is a cross-sectional view taken along line A'-A' of FIG. 2.

Preferably, as shown in FIG. 3, in the embodiment of the disclosure, an oil storage cavity 200 is provided inside the outer casing 10, with the oil storage cavity located above the atomization cavity 100, and two ends of the top of the atomization cavity 100 each are provided with an oil supply channel 140, oil inlet ends 141 of the two oil supply channels 140 each are in communication with the oil storage cavity 200, oil outlet ends 142 of the two oil supply channels 140 are respectively connected to upper surfaces of two ends of the oil guiding cotton cloth layer 133, that is, the oil outlet ends 142 of the two oil supply channels 140 may be directly contacted with upper surfaces of the two ends of the oil guiding cotton cloth layer 133.

It can be understood that the cigarette oil placed in the oil storage cavity 200 is supplied to the upper surfaces of the two ends of the oil guiding cotton cloth layer through the oil supply channels 140, where the size of the oil supply channels 140 can be designed as actually needed, so that the oil guiding cotton cloth layer 133 can be rapidly and conveniently supplied with oil in use, and the oil content of the oil guiding cotton cloth layer 133 can reach a balanced distribution more easily.

Preferably, in the embodiment of the disclosure, a gas guiding channel 300 is provided inside the outer casing 10, in the middle of the oil storage cavity 200, and the gas guiding channel 300 is in communication with the gas outlet 110.

Preferably, in the embodiment of the disclosure, a first electrode 150 and a second electrode 160 are provided in the atomization cavity 100, the first electrode 150 is electrically connected to one end of the electric heating wire 132, and the second electrode 160 is electrically connected to the other end of the electric heating wire 132.

It can be understood that the above-mentioned first electrode 150 and second electrode 160 are respectively a positive electrode and a negative electrode, and are respectively correspondingly connected to a positive electrode and a negative electrode of a battery through pins, and are also respectively connected with two ends of the electric heating wire 132 through corresponding positive electrode pin and negative electrode pin, that is, the positive electrode pin is connected to one end of the electric heating wire 132 and the negative electrode pin is connected to the other end of the electric heating wire 132 for supplying power to the electric heating wire 132 to cause the electric heating wire 132 to generate heat.

Figure 4:
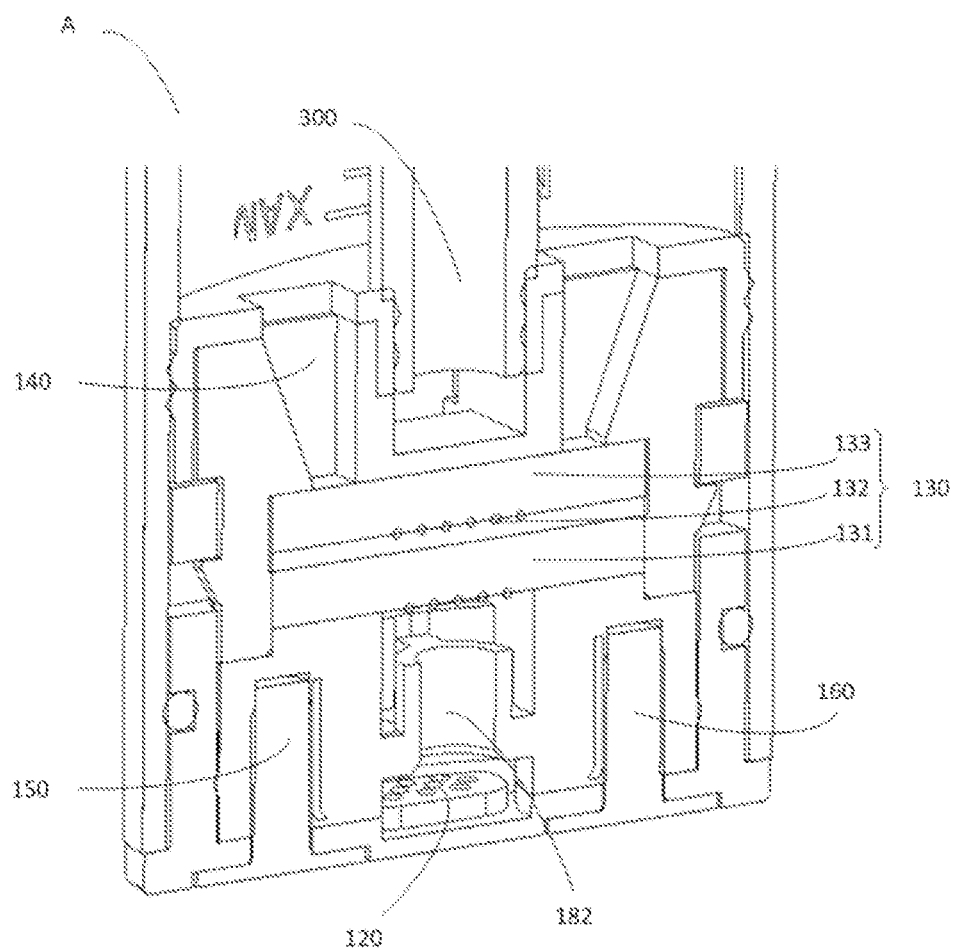
FIG. 4 is a partial enlarged view of A in FIG. 3.
Figure 5:
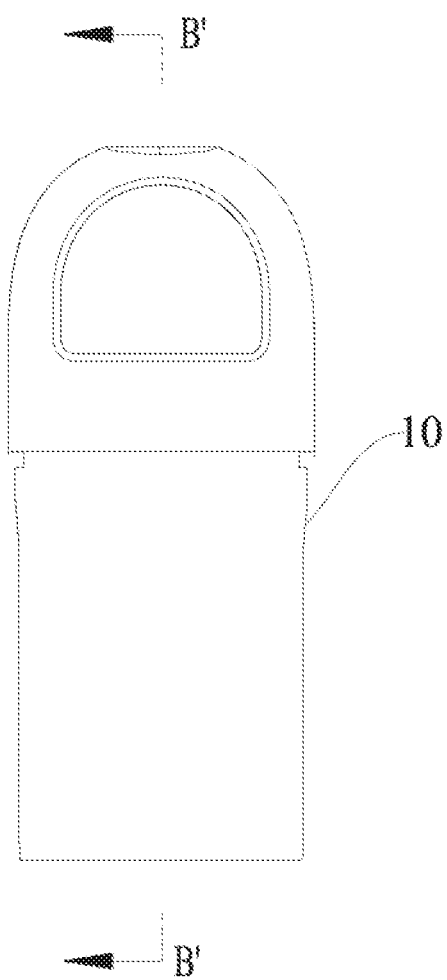
FIG. 5 is a front view of an electronic cigarette atomizer of an embodiment of the disclosure.
Figure 6:
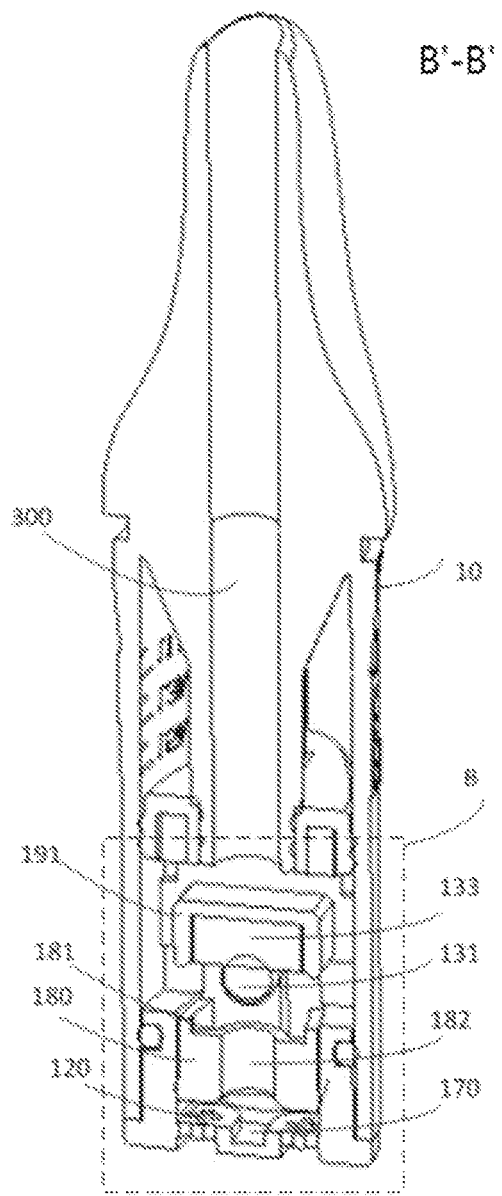
FIG. 6 is a cross-sectional view taken along line B'-B' of FIG. 5.
Figure 7:
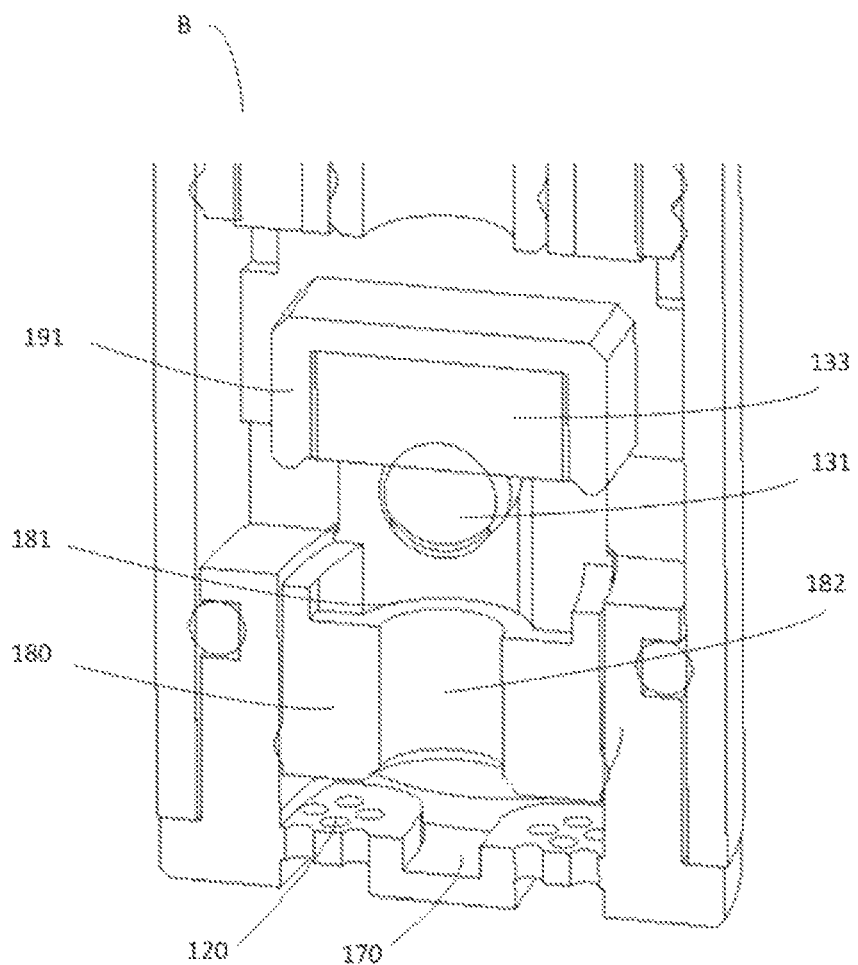
FIG. 7 is a partial enlarged view of B in FIG. 6.
Figure 8:
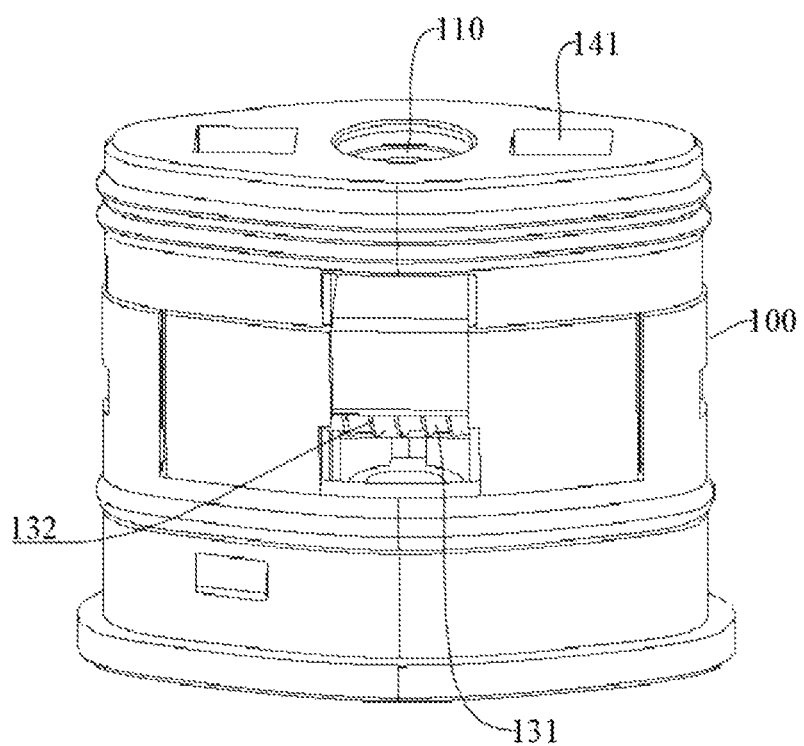
FIG. 8 is an isometric view of an atomization cavity of an embodiment of the disclosure.
Figure 9:
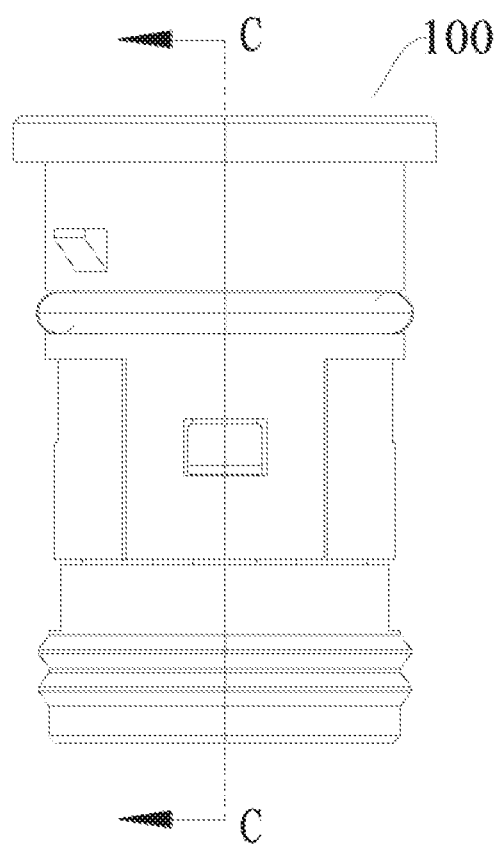
FIG. 9 is a left view of an atomization cavity of an embodiment of the disclosure.
Figure 10:
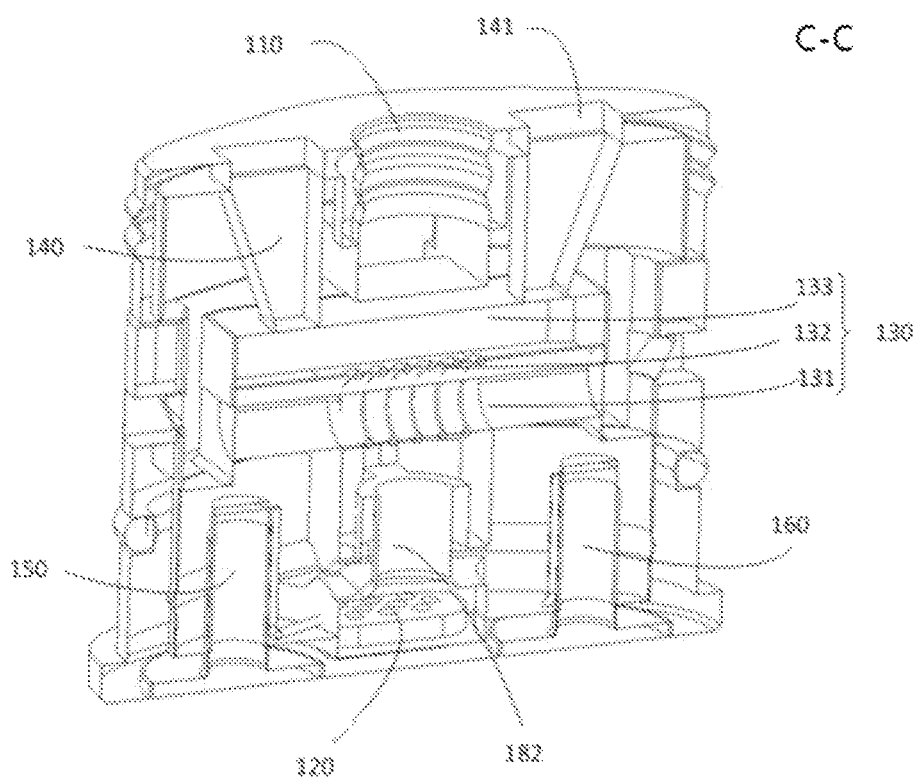
FIG. 10 is a cross-sectional view taken along line C-C of FIG. 9.
Figure 11:
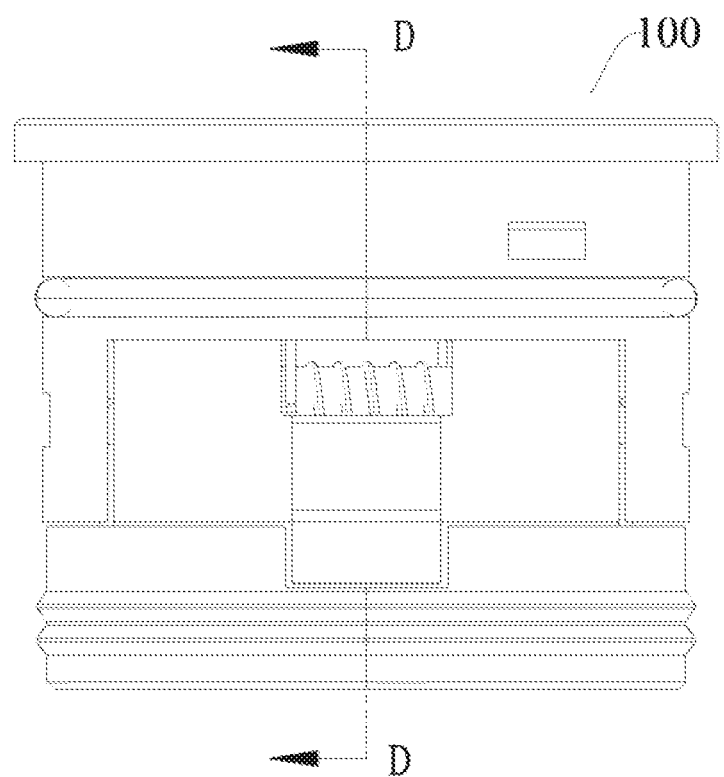
FIG. 11 is a front view of an atomization cavity of an embodiment of the disclosure.
Figure 12:
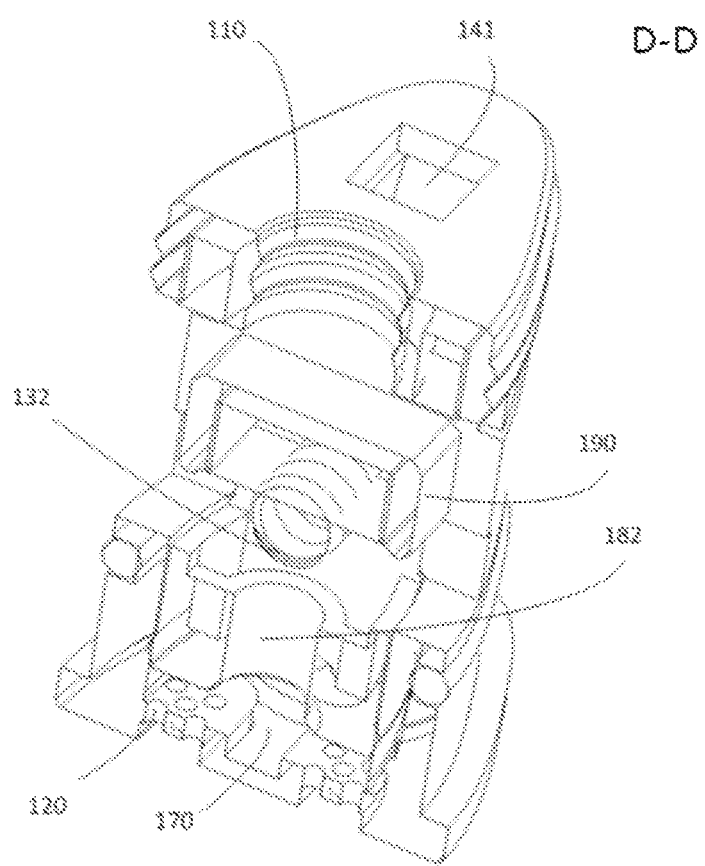
FIG. 12 is a cross-sectional view taken along line D-D of FIG. 11.
Figure 13:
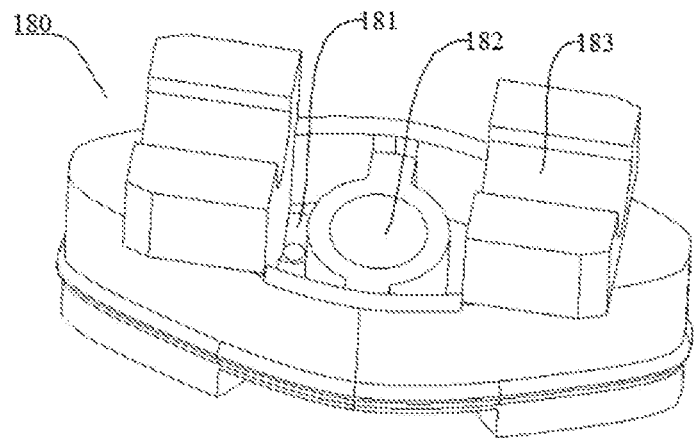
FIG. 13 is a structural schematic view of a lower base of an embodiment of the disclosure.
Figure 14:
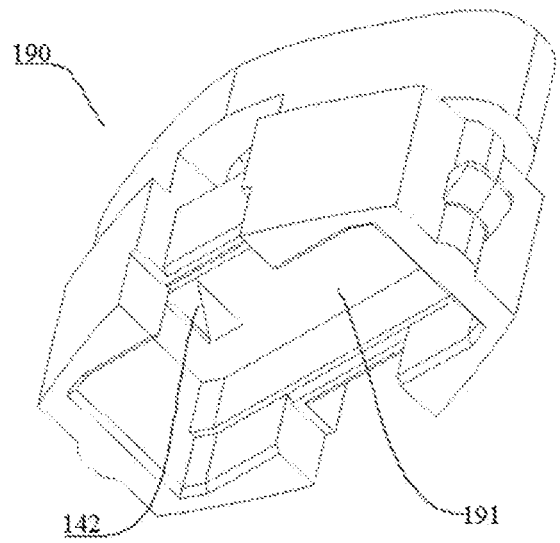
FIG. 14 is a structural schematic view of an upper base of an embodiment of the disclosure.

Preferably, as shown in FIGS. 4 and 7, in the embodiment of the disclosure, the gas inlet 120 comprises a plurality of micropores provided at the bottom end of the atomization cavity 100, and the cross-sectional area of each micropore is less than or equal to 0.785 mm$^2$. A first groove 170 is provided in a middle of an inner side of a bottom end of the atomization cavity 100.

Further, as shown in FIGS. 8 to 14, a lower base 180 is provided in the atomization cavity 100, the lower base configured for supporting the atomization assembly 130.

Further, a second groove 181 and a hollow channel 182 communicating the second groove 181 with the first groove 170 are provided in the middle of the lower base 180 and located below the atomization assembly 130, and a gas flow channel is provided between the bottom of the hollow channel 182 and the gas inlet 120.

Further, an upper base 190 is provided inside the atomization cavity 100, with the upper base 190 located above the lower base 180, the atomization assembly 130 is fixed between the upper base 190 and the lower base 180, and there are gas flow channels communicating with each other between two sides of the upper base 190 and inner walls of the atomization cavity 100, between the top of the upper base 190 and the gas outlet 110, and between the bottom of the upper base 190 and the top of the second groove 181.

Preferably, a first clamping slot 183 is provided at two ends of the top of the lower base 180, and two ends of the oil guiding cotton swab 131 are erected on the first clamping slot 183. The first clamping slot 183 is an arc-shaped clamping slot.

Preferably, the upper base 190 is provided with a second clamping slot 191 for accommodating the oil guiding cotton cloth layer 133. It should be noted that the oil supply channel 140 runs through the upper base 190, extending to the second clamping slot 191 such that the oil outlet end 141 is in contact with the upper surface of the oil guiding cotton cloth layer 133.

It should be noted that when the electronic cigarette atomizer is used, the gas, from the micropores at the bottom, enters the atomization cavity 100, may pass through the hollow channel and the second groove 181 in the middle of the lower base 180 to directly reach between the upper base 190 and the lower base 180, scatter the smoke generated by the atomization assembly 130 between the upper base 190 and the lower base 180 from the middle to the gas flow channel between the two sides of the upper base 190 and the inner walls of the atomization cavity 100, then pass through the gas flow channel between the top of the upper base 190 and the gas outlet 110, the gas outlet 110 and the gas guiding channel 300 to discharge to a suction nozzle, and in this way, the temperature of the smoke can be appropriately reduced, thereby avoiding the hot smoke from directly rushing to the mouth, where the taste is mild and moderate, and the mouth will not be burned.

The condensate liquid generated by a part of the smoke in the gas outlet 110 and the gas guiding channel 300 liquidized by cooling will first pass through the top of the upper base 190, a part of the condensate liquid will then flow from two sides of the upper base 190 to the inside of the second groove 181, and when the second groove 181 is full of liquid, it will continue to flow toward the first groove 170, and when the first groove 170 is full of liquid, it flows to the gas inlet micropores, and since the cross-sectional area of the single gas inlet micropore is 0.785 mm$^2$, the condensate liquid will first form an oil film on the micropores, which functions to further block the condensate liquid, thus avoiding the smoke condensate liquid from flowing directly into the battery connected to the bottom of the atomizer, influencing the performance of the battery.

The disclosure further provides an electronic cigarette, comprising the above-mentioned atomizer.

In summary, compared with the prior art, the electronic cigarette atomizer and electronic cigarette of the disclosure bring about the following beneficial effects:

(1) The electronic cigarette atomizer of the disclosure has a simple structure and a reasonable design, and the atomization assembly of the electronic cigarette atomizer comprises an oil guiding cotton swab, an electric heating wire wound around outer periphery of the oil guiding cotton swab, and an oil guiding cotton cloth layer covering the top of the oil guiding cotton swab; and the oil guiding cotton swab can absorb cigarette oil from the entire section of the above oil guiding cotton cloth layer, such that the entire section of the oil guiding cotton swab can supply oil to the electric heating wire in a balanced manner, and the oil guiding cotton cloth layer and the oil guiding cotton swab can also simultaneously supply oil to the electric heating wire. The "number of oil-containing molecules on the oil supply contact surface" required by normal working is YL, which is a product of the oil supply contact area S and the number L of oil-containing molecules per unit area, that is, YL=S*L. The oil content of the oil guiding cotton cloth layer and the oil guiding cotton swab of the atomization assembly of the electronic cigarette atomizer easily reaches a balanced distribution on the one hand, and the oil supply contact area S for the electric heating wire is also increased on the other hand, and the oil is supplied by adhering to the surface of the electric heating wire in multiple directions at close-range, the entire section of the electric heating wire is supplied with oil in a balanced and rapid manner. In this way, not only the number L of oil-containing molecules per unit area of the oil guiding cotton cloth layer and the oil guiding cotton swab is reduced accordingly, effectively reducing the risk of oil leakage, but also the surface heating temperature of the entire section of the electric heating wire is balanced, effectively solving the problem of scorching the cotton and cigarette oil, thereby effectively solving the problem of poor taste of atomized cigarette oil.

(2) Further, with the electronic cigarette atomizer of the disclosure, an oil storage cavity is provided inside the outer casing, with the oil storage cavity located above the atomization cavity, two ends of the top of the atomization cavity each are provided with an oil supply channel, such that top ends of the two oil supply channels each are in communication with the oil storage cavity, and bottom ends of the two oil supply channels are respectively connected with upper surfaces of two ends of the oil guiding cotton cloth layer, such that oil is supplied to the oil guiding cotton cloth layer rapidly and conveniently in use, and the oil content of the oil guiding cotton cloth layer easily reaches a balanced distribution.

(3) Further, with the electronic cigarette atomizer of the disclosure, a number of micropores are provided at a bottom end of the atomization cavity as gas inlets, a lower base is provided inside the atomization cavity, a second groove and a hollow channel communicating the second groove with the first groove are provided in the middle of the lower base and located below the atomization assembly, and a gas flow channel is provided between the bottom of the hollow channel and the gas inlet, there are gas flow channels communicating with each other between two sides of the upper base and inner walls of the atomization cavity, between the top of the upper base and the gas outlet, and between the bottom of the upper base and the top of the second groove, so that the gas, from the micropores at the bottom, passes through the hollow channel and the second groove in the middle of the lower base, scatters the smoke generated by the atomization assembly between the upper base and the lower base from the middle to the gas flow channel between the two sides of the upper base and the inner walls of the atomization cavity, and then passes through the gas flow channel between the top of the upper base and the gas outlet, the gas outlet and the gas guiding channel to discharge to a suction nozzle, and in this way, the temperature of the smoke can be appropriately reduced, thereby avoiding the hot smoke from directly rushing to the mouth, where the taste is mild and moderate and the mouth will not be burned.

(4) Further, with the electronic cigarette atomizer of the disclosure, the first groove, the second groove, and the upper base are provided, condensate liquid generated by a part of the smoke in the gas outlet and the gas guiding channel liquidized by cooling will first pass through the top of the upper base, a part of the condensate liquid will then flow from two sides of the upper base to the inside of the second groove, and when the second groove is full of liquid, it will continue to flow toward the first groove, and when the first groove is full of liquid, it flows to the gas inlet micropores, and since the cross-sectional area of the single gas inlet micropore is ≤0.785 mm², the condensate liquid will first form an oil film on the micropores, which functions to further block the condensate liquid.

In summary, with the special structure, the disclosure has the above-mentioned advantages and practical values, and there is no similar method disclosed or used in the similar products, and thus the disclosure is innovative, and the disclosure brings about good and practical effects, has multiple enhanced functions over the prior art, and thus is more suitable for practical use, and the disclosure has wide industrial values.

Although terms for structures are used pretty much above, such as "outer casing", "atomization cavity", and "oil guiding cotton cloth layer", the possibility of using other terms is not excluded. These terms are only used to more easily describe and explain the essence of the disclosure; and it is against the spirit of the disclosure if these terms are construed as any of the additional limitations.

What described above are only specific embodiments of the disclosure, and the scope of protection of the disclosure is not limited thereto, and changes or substitutions readily conceived by any skilled person familiar with the technique in the art within the technical scope of the disclosure should be covered by the scope of protection of the disclosure. Therefore, the scope of protection of the disclosure should be determined by the scope of protection of the claims.

The invention claimed is:

1. An electronic cigarette atomizer, comprising: an outer casing, wherein the outer casing is provided inside with an atomization cavity, a gas outlet is provided at a top end of the atomization cavity, and a gas inlet is provided at a bottom end of the atomization cavity, an atomization assembly is provided in the atomization cavity, and the atomization assembly comprises an oil guiding cotton swab, an electric heating wire wound around outer periphery of the oil guiding cotton swab, and an oil guiding cotton cloth layer covering a top of the oil guiding cotton swab,
  wherein the gas inlet comprises a plurality of micropores provided at the bottom end of the atomization cavity, a cross-sectional area of each micropore is less than or equal to 0.785 mm²; and a first groove is provided in a middle of an inner side of the bottom end of the atomization cavity,
  a lower base is provided in the atomization cavity, the lower base configured for supporting the atomization assembly,
  a second groove and a hollow channel configured to enable the second groove in fluid communication with the first groove are provided in a middle of the lower base and located below the atomization assembly, and a gas flow channel is provided between a bottom of the hollow channel and the gas inlet.

2. The electronic cigarette atomizer according to claim 1, wherein an oil storage cavity is provided inside the outer casing, with the oil storage cavity located above the atomization cavity, two ends of a top of the atomization cavity each are provided with an oil supply channel, oil inlet ends of two oil supply channels each are in fluid communication with the oil storage cavity, and oil outlet ends of the two oil supply channels are respectively connected with upper surfaces of two ends of the oil guiding cotton cloth layer.

3. The electronic cigarette atomizer according to claim 2, wherein a gas guiding channel is provided inside the outer casing, with gas guiding channel located in a middle of the oil storage cavity, and the gas guiding channel is in fluid communication with the gas outlet.

4. The electronic cigarette atomizer according to claim 1, wherein a first electrode and a second electrode are provided in the atomization cavity, the first electrode is electrically connected to one end of the electric heating wire, and the second electrode is electrically connected to other end of the electric heating wire.

5. The electronic cigarette atomizer according to claim 1, wherein an upper base is provided inside the atomization cavity, with the upper base located above the lower base, the atomization assembly is fixed between the upper base and the lower base, and gas flow channels in fluid communication with each other are provided between two sides of the upper base and inner walls of the atomization cavity, between a top of the upper base and the gas outlet, and between a bottom of the upper base and a top of the second groove.

6. The electronic cigarette atomizer according to claim 5, wherein a first clamping slot is provided at two ends of a top of the lower base, and two ends of the oil guiding cotton swab are erected on the first clamping slot; and the upper base is provided with a second clamping slot for accommodating the oil guiding cotton cloth layer.

7. An electronic cigarette, comprising the atomizer according to claim 1.

8. The electronic cigarette according to claim 7, wherein an oil storage cavity is provided inside the outer casing, with the oil storage cavity located above the atomization cavity, two ends of a top of the atomization cavity each are provided with an oil supply channel, oil inlet ends of two oil supply channels each are in fluid communication with the oil storage cavity, and oil outlet ends of the two oil supply channels are respectively connected with upper surfaces of two ends of the oil guiding cotton cloth layer.

9. The electronic cigarette according to claim 8, wherein a gas guiding channel is provided inside the outer casing, with gas guiding channel located in a middle of the oil storage cavity, and the gas guiding channel is in fluid communication with the gas outlet.

10. The electronic cigarette according to claim 7, wherein a first electrode and a second electrode are provided in the atomization cavity, the first electrode is electrically connected to one end of the electric heating wire, and the second electrode is electrically connected to other end of the electric heating wire.

\* \* \* \* \*